United States Patent
Pascaly et al.

(10) Patent No.: US 10,428,035 B2
(45) Date of Patent: Oct. 1, 2019

(54) PROCESS FOR THE EPOXIDATION OF AN OLEFIN

(71) Applicants: EVONIK DEGUSSA GMBH, Essen (DE); THYSSENKRUPP INDUSTRIAL SOLUTIONS AG, Essen (DE)

(72) Inventors: Matthias Pascaly, Frankfurt (DE); Manfred Bärz, Freigericht (DE); Marc Brendel, Bruchköbel (DE); Robert Jahn, Rodenbach (DE); Jürgen Schemel, Bad Soden (DE); Michael Dopfer, Sulzbach (DE)

(73) Assignees: Evonik Degussa GmbH, Essen (DE); thyssenkrupp Industrial Solutions AG, Essen (DE)

( * ) Notice: Subject to any disclaimer, the term of this patent is extended or adjusted under 35 U.S.C. 154(b) by 0 days.

(21) Appl. No.: 15/778,337

(22) PCT Filed: Nov. 1, 2016

(86) PCT No.: PCT/EP2016/076268
§ 371 (c)(1),
(2) Date: May 23, 2018

(87) PCT Pub. No.: WO2017/089074
PCT Pub. Date: Jun. 1, 2017

(65) Prior Publication Data
US 2018/0354923 A1    Dec. 13, 2018

(30) Foreign Application Priority Data
Nov. 26, 2015 (EP) .................................... 15196528

(51) Int. Cl.
| | | |
|---|---|---|
| *C07D 301/12* | (2006.01) | |
| *B01J 8/04* | (2006.01) | |
| *B01J 19/24* | (2006.01) | |
| *B01J 29/89* | (2006.01) | |
| *C07D 303/04* | (2006.01) | |

(52) U.S. Cl.
CPC .......... *C07D 301/12* (2013.01); *B01J 8/0492* (2013.01); *B01J 19/2475* (2013.01); *B01J 29/89* (2013.01); *B01J 2219/0027* (2013.01); *B01J 2219/00707* (2013.01); *B01J 2219/32279* (2013.01); *C07D 303/04* (2013.01)

(58) Field of Classification Search
CPC ...... C07D 301/12; C07D 303/04; B01J 29/89; B01J 8/0492; B01J 19/2475; B01J 2219/0027; B01J 2219/32279; B01J 2219/00707
USPC ....................................................... 549/531
See application file for complete search history.

(56) References Cited

U.S. PATENT DOCUMENTS

| | | |
|---|---|---|
| 4,308,409 A | 12/1981 | Wu et al. |
| 5,274,140 A | 12/1993 | Venturello et al. |
| 5,591,875 A | 1/1997 | Chang et al. |
| 5,599,956 A | 2/1997 | Pujado et al. |
| 6,372,924 B2 | 4/2002 | Thiele |
| 6,673,950 B1 | 1/2004 | Teles et al. |
| 6,861,042 B2 | 3/2005 | Korl et al. |
| 7,169,945 B2 | 1/2007 | Haas et al. |
| 7,173,143 B2 | 2/2007 | Bender et al. |
| 7,601,263 B2 | 10/2009 | Ebert et al. |
| 7,658,893 B2 | 2/2010 | Bassler et al. |
| 7,670,572 B2 | 3/2010 | Porscha et al. |
| 7,833,498 B2 | 11/2010 | Goebbel et al. |
| 7,863,211 B2 | 1/2011 | Strebelle et al. |
| 8,545,673 B2 | 10/2013 | Dietz et al. |
| 9,539,549 B2 | 1/2017 | Haensel et al. |
| 10,053,438 B2 | 8/2018 | Bolz et al. |
| 10,053,440 B2 | 8/2018 | Bolz et al. |
| 10,087,158 B2 | 10/2018 | Stock et al. |
| 10,100,024 B2 | 10/2018 | Stochniol et al. |
| 10,125,108 B2 | 11/2018 | Jahn et al. |
| 10,214,471 B2 | 2/2019 | Wiederhold et al. |
| 10,214,504 B2 | 2/2019 | Brendel et al. |
| 2003/0040637 A1 | 2/2003 | Hofen et al. |
| 2005/0245751 A1 | 11/2005 | Bender et al. |
| 2006/0014970 A1* | 1/2006 | Goebbel ............... B01J 8/20 549/529 |
| 2006/0058539 A1 | 3/2006 | Babler et al. |

(Continued)

FOREIGN PATENT DOCUMENTS

| | | |
|---|---|---|
| DE | 195 07 584 | 9/1996 |
| EP | 0 100 119 | 2/1984 |

(Continued)

OTHER PUBLICATIONS

International Search Report for PCT/EP2016/076268 filed Nov. 1, 2016.
Written Opinion of the International Searching Authority for PCT/EP2016/076268 filed Nov. 1, 2016.
International Preliminary Report on Patentability for PCT/EP2016/076268 filed Nov. 1, 2016.
European Search Report for EP 15 19 6528 filed Nov. 26, 2015.
International Search Report for PCT/EP2017/050236 filed Jan. 6, 2017, for copending U.S. Appl. No. 16/070,873.

(Continued)

*Primary Examiner* — Taylor V Oh
(74) *Attorney, Agent, or Firm* — Law Office of: Michael A. Sanzo, LLC

(57) ABSTRACT

In a process for the epoxidation of an olefin by continuously reacting the olefin with hydrogen peroxide in a methanol solvent on a fixed bed epoxidation catalyst comprising a titanium zeolite, the hydrogen peroxide is used as an aqueous hydrogen peroxide solution made by an anthraquinone process, the aqueous hydrogen peroxide solution is mixed with methanol to give a feed mixture and this feed mixture is filtered before being contacted with the fixed bed epoxidation catalyst.

11 Claims, No Drawings

(56) References Cited

U.S. PATENT DOCUMENTS

| | | | |
|---|---|---|---|
| 2007/0004926 A1* | 1/2007 | Schindler | C07D 301/12 549/531 |
| 2012/0142950 A1 | 6/2012 | Teles et al. | |
| 2015/0007951 A1 | 1/2015 | Dietz et al. | |
| 2017/0210718 A1 | 7/2017 | Stochinol et al. | |
| 2018/0002299 A1 | 1/2018 | Bolz et al. | |
| 2018/0002300 A1 | 1/2018 | Bolz et al. | |
| 2018/0030010 A1 | 2/2018 | Breitenbach et al. | |
| 2018/0030011 A1 | 2/2018 | Stock et al. | |
| 2018/0030012 A1 | 2/2018 | Stock et al. | |
| 2018/0057473 A1 | 3/2018 | Stock et al. | |
| 2018/0134676 A1 | 5/2018 | Jahn et al. | |
| 2018/0346432 A1 | 12/2018 | Hofen et al. | |
| 2018/0354878 A1 | 12/2018 | Wiederhold et al. | |
| 2018/0354923 A1 | 12/2018 | Pascaly et al. | |
| 2018/0370934 A1 | 12/2018 | Brendel et al. | |
| 2019/0023673 A1 | 1/2019 | Schmidt et al. | |

FOREIGN PATENT DOCUMENTS

| | | |
|---|---|---|
| EP | 0 230 949 | 8/1987 |
| EP | 0 659 473 | 6/1995 |
| EP | 0 757 045 | 2/1997 |
| EP | 1 247 806 | 10/2002 |
| EP | 1 489 074 | 12/2004 |
| WO | WO 02/085873 | 10/2002 |
| WO | WO 03/016296 | 2/2003 |
| WO | WO 03/018567 | 3/2003 |
| WO | WO 03/093255 | 11/2003 |
| WO | WO 2004/018088 | 3/2004 |
| WO | WO 2004/028962 | 4/2004 |
| WO | WO 2004/048335 | 6/2004 |
| WO | WO 2004/048354 | 6/2004 |
| WO | WO 2004/048355 | 6/2004 |
| WO | WO 2005/000827 | 1/2005 |
| WO | WO 2005/103024 | 11/2005 |
| WO | WO 2008/141734 | 11/2008 |
| WO | WO 2011/063937 | 6/2011 |
| WO | WO 2016/016070 | 2/2016 |

OTHER PUBLICATIONS

Written Opinion of the International Searching Authority for PCT/EP2017/050236 filed Jan. 6, 2017, for copending U.S. Appl. No. 16/070,873.

International Preliminary Report on Patentability for PCT/EP2017/050236 filed Jan. 6, 2017, for copending U.S. Appl. No. 16/070,873.

Chowdhury, et al, "Recovery of Homogeneous Polyoxometallate Catalysts from Aqueous and Organic Media by a Mesoporous Ceramic Membrane without Loss of Catalytic Activity," *Chem. Eur. J.* 12(11):3061-3066 (Apr. 2006).

Guojie, et al., "Factors Affecting Propylene Epoxidation Catalyzed by Reaction-Controlled Phase-Transfer Catalyst," *Chinese Journal of Catalysis* 26:1005-1010 (Nov. 2005).

Kaur, et al., "Poloxometalate-catalysed epoxidation of propylene with hydrogen peroxide: microemulsion versus biphasic process," *Catalysis Communications* 5(11): 709-713 (Nov. 2004).

Li, et al., "Influence of composition of heteropolyphosphatotungstate catalyst on epoxidation of propylene," *Journal of Molecular Catalysis A: Chemical* 218(2):247-252 (Aug. 2004).

Luthra, et al., "Homogeneous phase transfer catalyst recovery and re-use using solvent resistant membranes," *Journal of Membrane Science* 201:65-75 (2002).

Venturello, et al., "A New, Effective Catalytic System for Epoxidation of Olefins by Hydrogen Peroxide under Phase-Transfer Conditions," *J. Org. Chem.* 48:3831-3833 (1983).

U.S. Appl. No. 15/329,626, filed Jan. 26, 2017, US-2017/0210718 A1, Jul. 27, 2017, Stochinol.

U.S. Appl. No. 15/570,167, filed Oct. 15, 2017, US-2018/0134676 A1, May 27, 2018, Jahn.

U.S. Appl. No. 15/778,318, filed May 23, 2018, Brendel.

U.S. Appl. No. 15/778,425, filed May 23, 2018, Hofen.

U.S. Appl. No. 15/778,562, filed May 23, 2018, Wiederhold.

U.S. Appl. No. 16/070,873, filed Jul. 18, 2018, Schmidt.

Ullmann Encyclopedia of Industrial Chemistry, online edition 2013, entry "propene," DOI 10.1002/14356007.a22_211.pub3.

U.S. Appl. No. 16/086,309, filed Sep. 18, 2018, Wöll.

U.S. Appl. No. 16/302,099, filed Nov. 15, 2018, Wiederhold.

* cited by examiner

PROCESS FOR THE EPOXIDATION OF AN OLEFIN

CROSS REFERENCE TO RELATED APPLICATIONS

The present application is US national stage of international application PCT/EP2016/076268, which had an international filing date of Nov. 1, 2016, and which was published on Jun. 1, 2017. Priority is claimed to European application EP 15196528.2, filed on Nov. 26, 2015.

FIELD OF THE INVENTION

The present invention relates to a process for the epoxidation of an olefin by continuously reacting the olefin with hydrogen peroxide in a methanol solvent on a fixed bed epoxidation catalyst.

BACKGROUND OF THE INVENTION

The liquid phase epoxidation of olefins with hydrogen peroxide catalyzed by a fixed bed titanium silicalite catalyst is known from EP 0 100 119 A1. The reaction is usually carried out in a methanol solvent to achieve high reaction rate and product selectivity. Continuous epoxidation is achieved by passing a mixture comprising olefin, hydrogen peroxide and methanol through a fixed bed of the epoxidation catalyst, as described in WO 99/28029, WO 01/10855 and EP 1 085 017 A1.

SUMMARY OF THE INVENTION

It has now been found that during extended operation of such a continuous epoxidation, using an aqueous hydrogen peroxide solution from an anthraquinone process, deposits can form on the catalyst which are not removed by usual catalyst regeneration procedures of washing with methanol solvent or heating. These deposits reduce catalyst activity and may cause liquid maldistribution in the catalyst fixed bed, leading to an uneven temperature profile in the fixed bed which impairs selectivity for the epoxide. When a tube bundle reactor is used and a mixture comprising hydrogen peroxide and methanol is distributed to the tubes through orifices of a liquid distributor, similar deposits can form or accumulate at the orifices and blocking of the orifices by the deposits can lead to maldistribution of liquid to the individual tubes.

It has further been found that formation of such deposits may be reduced or avoided by mixing the hydrogen peroxide solution with methanol and filtering the resulting mixture before using it in the epoxidation reaction.

Subject of the invention is therefore a process for the epoxidation of an olefin by continuously reacting the olefin with hydrogen peroxide in a methanol solvent on a fixed bed epoxidation catalyst comprising a titanium zeolite, where hydrogen peroxide is used as an aqueous hydrogen peroxide solution made by an anthraquinone process, the aqueous hydrogen peroxide solution is mixed with methanol to give a feed mixture and this feed mixture is filtered before being contacted with the fixed bed epoxidation catalyst.

DETAILED DESCRIPTION OF THE INVENTION

In the process of the invention an olefin is reacted with hydrogen peroxide in a methanol solvent on a fixed bed epoxidation catalyst comprising a titanium zeolite.

The olefin is preferably an unbranched olefin, more preferably an unbranched C2-C6 olefin. The olefin may be substituted, as for example in allyl chloride. Most preferably, the olefin is propene. Propene may be used mixed with propane, preferably with a molar ratio of propane to propene of from 0.001 to 0.15 and more preferably of from 0.08 to 0.12.

The hydrogen peroxide used in the process of the invention is an aqueous hydrogen peroxide solution made by an anthraquinone process. The anthraquinone process uses a working solution comprising at least one 2-alkylanthraquinone, 2-alkyltetrahydroanthraquinone or a mixture of both, referred to as quinones in the following, and at least one solvent for dissolving the quinone and the hydroquinone. The 2-alkylanthraquinone is preferably 2-ethylanthraquinone (EAQ), 2-amylanthraquinone (AAQ) or 2-(4-methylpentyl)-anthraquinone (IHAQ) and more preferably a mixture of EAQ with AAQ and/or IHAQ where the molar fraction of quinones carrying an ethyl group is from 0.05 to 0.95. The working solution preferably further comprises the corresponding 2-alkyltetrahydroanthraquinones and the ratio of 2-alkyltetrahydroanthraquinones plus 2-alkyltetrahydroanthrahydroquinones to 2-alkylanthraquinones plus 2-alkylanthrahydroquinones is preferably maintained in the range of from 1 to 20 by adjusting the conditions of the hydrogenating and regenerating steps used in the anthraquinone process. The working solution preferably comprises a mixture of alkylbenzenes having 9 or 10 carbon atoms as solvent for anthraquinones and at least one polar solvent selected from diisobutylcarbinol (DiBC), methylcyclohexylacetate (MCA), trioctylphosphate (TOP), tetrabutylurea (TBU) and N-octylcaprolactam as solvent for anthrahydroquinones, DiBC, MCA and TOP being preferred and TOP being most preferred.

The anthraquinone process is a cyclic process, comprising a hydrogenation stage, where hydrogen is reacted with working solution in the presence of a hydrogenation catalyst to convert at least part of the quinone to the corresponding hydroquinone, a subsequent oxidation stage, where the hydrogenated working solution containing hydroquinone is reacted with oxygen to form hydrogen peroxide and quinone, and an extraction stage, where hydrogen peroxide is extracted from the oxidized working solution with water to provide an aqueous solution of hydrogen peroxide, with the extracted working solution being returned to the hydrogenation stage to complete a reaction cycle.

In the hydrogenation stage, the working solution is reacted with hydrogen in the presence of a heterogeneous hydrogenation catalyst. During the reaction all or a part of the quinones are converted to the corresponding hydroquinones. All hydrogenation catalysts known from the prior art for the anthraquinone cyclic process can be used as catalysts in the hydrogenation stage. Noble metal catalysts containing palladium as the principal component are preferred. The catalysts can be used as a fixed bed catalysts or as a suspended catalyst and suspended catalysts can be either unsupported catalysts, such as palladium black, or supported catalysts, with suspended supported catalysts being preferred. $SiO_2$, $TiO_2$, $Al_2O_3$ and mixed oxides thereof, as well as zeolites, $BaSO_4$ or polysiloxanes, are can be used as support materials for fixed-bed catalysts or supported suspended catalysts, with $TiO_2$ and $SiO_2/TiO_2$ mixed oxides being preferred. Catalysts in the form of monolithic or honeycombed moldings, the surface of which is coated with the noble metal, can also be used. Hydrogenation can be carried out in stirred-tank reactors, tube reactors, fixed-bed reactors, loop reactors or air-lift reactors which can be equipped with devices for distributing hydrogen in the working solution, such as static mixers or injection nozzles. Preferably, a tube reactor with a recycle and a Venturi nozzle for injecting hydrogen into the reactor feed as known from WO 02/34668 is used. Hydrogenation is carried out at a temperature of from 20 to 100° C., preferably 45 to 75° C., and a pressure of from 0.1 MPa to 1 MPa, preferably 0.2 MPa to 0.5 MPa. The hydrogenation is preferably performed in such a way that essentially all hydrogen introduced into the hydrogenation reactor is consumed in a single pass through the reactor. The ratio between hydrogen and working solution fed to the hydrogenation reactor is preferably chosen to convert between 30 and 80% of the quinones to the corresponding hydroquinones. If a mixture of 2-alkylanthraquinones and 2-alkyltetrahydroanthraquinones is used, the ratio between hydrogen and working solution is preferably chosen so that only the 2-alkyltetrahydroanthraquinones are converted to hydroquinones and the 2-alkylanthraquinones remain in the quinone form.

In the oxidation stage, the hydrogenated working solution from is reacted with an oxygen-containing gas, preferably with air or with oxygen enriched air. All oxidation reactors known from the prior art for the anthraquinone process can be used for the oxidation, bubble columns operated in co-current being preferred. The bubble column can be free from internal devices, but preferably contains distribution devices in the form of packings or sieve plates, most preferably sieve plates in combination with internal coolers. Oxidation is carried out at a temperature of from 30 to 70° C., preferably from 40 to 60° C. Oxidation is preferably performed with an excess of oxygen to convert more than 90%, preferably more than 95%, of the hydroquinones to the quinone form.

In the extraction stage, the oxidized working solution containing dissolved hydrogen peroxide is extracted with an aqueous solution to provide an aqueous hydrogen peroxide solution and an extracted oxidized working solution containing essentially no hydrogen peroxide. Deionized water, which may optionally contain additives for stabilizing hydrogen peroxide, adjusting the pH and/or corrosion protection, is preferably used for extracting the hydrogen peroxide. The aqueous solution used for extracting hydrogen peroxide from the working solution preferably comprises phosphoric acid in a concentration of from 50 to 500 ppm by weight. Extraction is preferably carried out in a counter-current continuous extraction column, sieve-plate columns being most preferred. The aqueous hydrogen peroxide solution obtained by extraction may be used directly in the epoxidation or may be concentrated by distilling off water at reduced pressure, preferably to a concentration of from 40 to 70% by weight. The aqueous hydrogen peroxide solution obtained by extraction may also be purified, preferably by washing with a solvent, which is preferably a solvent comprised in the working solution.

The anthraquinone process preferably comprises at least one additional stage for regenerating the working solution, where by-products formed in the process are converted back to quinones. Regeneration is carried out by treating hydrogenated working solution with alumina or sodium hydroxide, preferably using a side stream to the cyclic process. In addition to regeneration of hydrogenated working solution, extracted oxidized working solution may be regenerated in a side stream using alumina, sodium hydroxide or an organic amine. Suitable methods for regenerating the working solution on an anthraquinone process are known from the prior art.

In the process of the invention, the olefin is reacted with hydrogen peroxide in a methanol solvent. Methanol can be used as a technical grade methanol, a solvent stream recovered in the work-up of the epoxidation reaction mixture or a mixture of both. The methanol may comprise other solvents in minor amounts, such as ethanol, with the amount of such other solvents preferably being less than 2% by weight. The methanol solvent is preferably used in the epoxidation in a weight ratio of 0.5 to 20 relative to the weight of the aqueous hydrogen peroxide solution.

The olefin is preferably used at a molar ratio of olefin to hydrogen peroxide of from 1.1:1 to 30:1, more preferably 2:1 to 10:1 and most preferably 3:1 to 5:1. The epoxidation reaction is preferably carried out at a temperature of 30 to 80° C., more preferably at 40 to 60° C. The epoxidation reaction is preferably carried out at a pressure that is higher than the vapor pressure of the olefin at the reaction temperature in order to maintain the olefin dissolved in the methanol solvent or present as a separate liquid phase. The epoxidation reaction is preferably carried out with addition of ammonia to improve epoxide selectivity as described in EP 0 230 949 A2. Ammonia is preferably added in an amount of from 100 to 3000 ppm based on the weight of hydrogen peroxide.

When the olefin is propene, the pressure in the epoxidation reaction is preferably from 1.9 to 5.0 MPa, more preferably 2.1 to 3.6 MPa and most preferably 2.4 to 2.8 MPa. Propene is preferably used in an excess sufficient to maintain an additional liquid phase rich in propene throughout the epoxidation reaction. Using an excess of propene at a high pressure provides high reaction rate and hydrogen peroxide conversion and at the same time high selectivity for propene oxide.

The olefin is continuously reacted with hydrogen peroxide on a fixed bed epoxidation catalyst comprising a titanium zeolite. Suitable titanium zeolites contain titanium atoms on silicon lattice positions. Preferably, a titanium silicalite catalyst is used, preferably with an MFI or MEL crystal structure. Most preferably a titanium silicalite 1 catalyst with MFI structure as known from EP 0 100 119 A1, is used. The titanium silicalite catalyst is preferably employed as a shaped catalyst in the form of granules, extrudates or shaped bodies. The shaped catalyst may contain 1 to 99% of a binder or carrier material, all binders and carrier materials being suitable that do not react with hydrogen peroxide or with propene oxide under the reaction conditions employed for the epoxidation, silica being preferred as binder. Extrudates with a diameter of 1 to 5 mm are preferably used as fixed bed catalysts. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions.

The epoxidation is preferably carried out in a fixed bed reactor by passing a mixture comprising olefin, hydrogen peroxide and methanol over a fixed bed comprising a shaped titanium silicalite catalyst. The fixed bed reactor is preferably equipped with cooling means and cooled with a liquid cooling medium. When the olefin is propene, the temperature profile within this reactor is preferably maintained such that the cooling medium temperature of the cooling means is at least 40° C. and the maximum temperature within the catalyst bed is 60° C. at the most, preferably 55° C. The epoxidation reaction mixture is preferably passed through the catalyst bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) from 1 to 20 $h^{-1}$, preferably 1.3 to 15 $h^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15. When the olefin is propene, the epoxidation reaction is most preferably carried out with a catalyst fixed bed maintained in a trickle bed state at a pressure close to the vapor pressure of propene at the reaction temperature, using an excess of propene that provides a reaction mixture comprising two liquid phases, a methanol rich phase and a propene rich liquid phase. Two or more fixed bed reactors may be operated in parallel or in series in order to be able to operate the epoxidation process continuously when regenerating the epoxidation catalyst. Regeneration of the epoxidation catalyst can be carried out by calcination, by treatment with a heated gas, preferably an oxygen containing gas or by a solvent wash, preferably by the periodic regeneration described in WO 2005/000827. Different methods of regeneration may also be combined.

In the process of the invention, the aqueous hydrogen peroxide solution is mixed with methanol to give a feed mixture and this feed mixture is filtered before it is contacted with the fixed bed epoxidation catalyst. The feed mixture may comprise all or a part of the methanol used in the epoxidation reaction. Preferably, the aqueous hydrogen peroxide solution is mixed with at least 50% of the methanol used for reacting the olefin with hydrogen peroxide, more preferably with at least 80% of the methanol, to provide the feed mixture that is filtered.

The feed mixture is preferably filtered through a filter medium having an average pore size of from 0.1 to 50 µm, more preferably from 1 to 50 µm. Any filter medium can be used that is sufficiently stable to hydrogen peroxide and methanol and does not promote decomposition of hydrogen peroxide. Preferably, a filter medium made from aramide polymers, polyolefins, polyamides, fluorinated polymers, sintered metals or combinations thereof is used. Suitable filter media are commercially available from 3M and Pall. Most preferably, the filter medium is made from polypropylene or from the polyamide of 1,3-diaminobenzene and benzene-1,3-dicarboxylic acid available under the trade name Nomex®.

The filtered feed mixture is preferably mixed with the olefin before being contacted with the fixed bed epoxidation catalyst. Mixing may be carried out by turbulent flow in a feed line or in a dedicated mixer, such as a static mixer. Mixing may also be achieved by passing the filtered feed mixture, the olefin and optionally further feed streams through a layer of inert solid, such as a layer of glass beads, arranged upstream of the fixed bed epoxidation catalyst.

In a preferred embodiment of the invention, the fixed bed epoxidation catalyst is placed in the tubes of a vertically arranged tube bundle reactor and the filtered feed mixture is distributed to the top of these tubes through orifices of a liquid distributor. Feed streams and reaction conditions are preferably selected to maintain the catalyst bed in a trickle bed state as described above. Suitable liquid distributors are known from the prior art and are commercially available.

The olefin may be added to the feed mixture of aqueous hydrogen peroxide and methanol before this is filtered if the resulting mixture comprises a single liquid phase. Alternatively, the filtered feed mixture may be combined with the olefin before it is distributed to the top of the tubes. In a further alternative, the filtered feed mixture and the olefin may be distributed to the top of the tubes through orifices of two separate liquid distributors, which is preferred when the olefin is employed in an amount exceeding its solubility in the filtered feed mixture. Suitable liquid distributors for separately distributing two liquids to reaction tubes of a tube bundle reactor are known from the prior art, for example from WO 2005/025716.

The feed mixture is preferably filtered with a filter which comprises a filter medium and a gas separator upstream of the filter medium. The gas separator is purged with an inert gas. Suitable inert gases are nitrogen, noble gases, carbon dioxide and mixtures thereof, with nitrogen being preferred. The inert gas is used in an amount sufficient to maintain an oxygen concentration in the purge gas of less than 5% by volume. The amount of inert gas used for purging the gas separator may be regulated by measuring the oxygen concentration in the purge gas. The use of a gas separator purged with inert gas prevents the formation of a flammable gas phase in the filter, the gas containing oxygen formed by decomposition of hydrogen peroxide.

The filter used for filtering the feed mixture preferably comprises a temperature sensor, a pressure sensor and a safety valve connected with a dump vessel, and the safety valve is opened for emptying the filter when the temperature or the pressure in the filter exceeds a preset safety limit. Suitable safety limits for the temperature or the pressure in the filter are 75° C. and 5 MPa. The dump vessel preferably contains an aqueous solution comprising a hydrogen peroxide stabilizer. Emptying the filter through a safety valve when the temperature or the pressure in the filter exceeds a safety limit prevents the runaway of a hydrogen peroxide decomposition in the filter which may lead to rupture of the filter casing and a subsequent release of methanol. Emptying the filter content to a dump vessel containing hydrogen peroxide stabilizer reduces hydrogen peroxide decomposition to a level that prevents a runaway of the decomposition that could lead to large volumes of flammable mixtures of oxygen and methanol vapor.

The olefin oxide formed by the epoxidation reaction can be separated from the epoxidation reaction mixture by methods known from the prior art, such as by distillation or extractive distillation. When the olefin is propene, propene oxide is preferably separated from the epoxidation reaction mixture by distillation after a pressure release stage which removes most of the non-reacted propene. The distillation is preferably carried out in at least two columns, operating the first column to provide a crude propene oxide overhead product containing from 20 to 60% of the methanol contained in the epoxidation reaction mixture and further purifying the overhead product by at least one additional distillation. The overhead product is preferably further purified by distilling off remaining propene and propane, followed by extractive distillation, most preferably using the extractive distillation method of WO 2004/048355 for additional removal of carbonyl compounds.

EXAMPLES

Example 1

Propene was continuously epoxidized with hydrogen peroxide in a methanol solvent in a tube bundle reactor with a fixed bed of a shaped titanium silicalite catalyst arranged inside the tubes. Liquid propene and a mixture of methanol and an aqueous hydrogen peroxide solution were distributed separately to the top of the tubes through orifices of a liquid distributor to provide a trickle flow in the fixed bed. The mixture was obtained by mixing methanol and a 70% by weight aqueous hydrogen peroxide solution, made by an anthraquinone process, at a weight ratio of 5:1. After 3 months of operation a white precipitate was observed in the liquid distributor and after a further 3 months of operation a blocking of orifices through which the mixture of hydrogen peroxide and methanol was distributed was observed.

Example 2

Example 1 was repeated, but the mixture of hydrogen peroxide and methanol was filtered through a filter made from polypropylene having a nominal pore size of 1 µm before passing it to the liquid distributor. During 12 months of operation no precipitate was observed in the liquid distributor and no blocking of orifices occurred.

The invention claimed is:

1. A process for the epoxidation of an olefin by continuously reacting the olefin with hydrogen peroxide in a methanol solvent on a fixed bed epoxidation catalyst comprising a titanium zeolite, wherein:
   a) hydrogen peroxide is used as an aqueous hydrogen peroxide solution made by an anthraquinone process;
   b) the aqueous hydrogen peroxide solution is mixed with methanol to give a feed mixture; and
   c) said feed mixture is filtered before being contacted with the fixed bed epoxidation catalyst.

2. The process of claim 1, wherein the aqueous hydrogen peroxide solution is mixed with at least 50% of the methanol used for reacting the olefin with hydrogen peroxide.

3. The process of claim 1, wherein the feed mixture is filtered through a filter medium having an average pore size of from 0.1 to 50 µm.

4. The process of claim 1, wherein the filter medium is selected from aramid polymers, polyolefins, polyamides, fluorinated polymers and sintered metals.

5. The process of claim 1, wherein the olefin is propene.

6. The process of claim 1, wherein the filtered feed mixture is mixed with the olefin before being contacted with the fixed bed epoxidation catalyst.

7. The process of claim 1, wherein the fixed bed epoxidation catalyst is placed in the tubes of a vertically arranged tube bundle reactor and the filtered feed mixture is distributed to the top of said tubes through orifices of a liquid distributor.

8. The process of claim 7 wherein the filtered feed mixture is combined with the olefin before being distributed to the top of the tubes.

9. The process of claim 7, wherein the filtered feed mixture and the olefin are distributed to the top of said tubes through orifices of two separate liquid distributors.

10. The process of claim 1, wherein the feed mixture is filtered with a filter comprising a filter medium and a gas separator upstream of said filter medium, and said gas separator is purged with an inert gas.

11. The process of claim 10, wherein the filter comprises a temperature sensor, a pressure sensor and a safety valve connected with a dump vessel, and the safety valve is opened for emptying the filter when the temperature or the pressure in the filter exceeds a preset safety limit.

* * * * *